(12) United States Patent
Gleason et al.

(10) Patent No.: US 9,526,536 B2
(45) Date of Patent: Dec. 27, 2016

(54) ARTICULATING ROD HOLDER

(71) Applicant: Spineology Inc., St. Paul, MN (US)

(72) Inventors: Joseph Gleason, Eagan, MN (US); Kyle Wolff, Cottage Grove, MN (US)

(73) Assignee: Spineology Inc., St. Paul, MN (US)

( * ) Notice: Subject to any disclaimer, the term of this patent is extended or adjusted under 35 U.S.C. 154(b) by 0 days.

(21) Appl. No.: 14/516,547

(22) Filed: Oct. 16, 2014

(65) Prior Publication Data
US 2015/0105832 A1    Apr. 16, 2015

Related U.S. Application Data

(60) Provisional application No. 61/891,745, filed on Oct. 16, 2013.

(51) Int. Cl.
*A61B 17/70* (2006.01)
(52) U.S. Cl.
CPC .................................. *A61B 17/7085* (2013.01)
(58) Field of Classification Search
CPC .................................. A61B 17/7083–17/7089
USPC ................................................. 606/86 A, 99
See application file for complete search history.

(56) References Cited

U.S. PATENT DOCUMENTS

| 7,967,826 | B2* | 6/2011 | Colleran | A61B 5/103 606/99 |
| 8,414,590 | B2* | 4/2013 | Oh | A61F 2/4611 606/86 A |
| 8,777,954 | B2* | 7/2014 | McLean | A61B 17/7032 606/86 A |
| 8,900,237 | B2* | 12/2014 | Ramsay | A61B 17/1735 606/104 |
| 2003/0208203 | A1* | 11/2003 | Lim | A61B 17/7083 606/86 A |
| 2005/0131419 | A1* | 6/2005 | McCord | A61B 17/7085 606/99 |
| 2005/0131420 | A1* | 6/2005 | Techiera | A61B 17/7002 606/99 |
| 2005/0192589 | A1* | 9/2005 | Raymond | A61B 17/7002 606/99 |
| 2006/0247630 | A1* | 11/2006 | Iott | A61B 17/701 606/86 A |
| 2007/0191836 | A1* | 8/2007 | Justis | A61B 17/7085 606/279 |
| 2008/0077138 | A1* | 3/2008 | Cohen | A61B 17/7083 606/86 A |
| 2008/0125788 | A1* | 5/2008 | Cohen | A61B 17/7085 606/104 |
| 2008/0312703 | A1* | 12/2008 | Hestad | A61B 17/7085 606/86 A |
| 2010/0249856 | A1* | 9/2010 | Iott | A61B 17/7085 606/86 A |
| 2011/0152942 | A1* | 6/2011 | Oh | A61B 17/7002 606/279 |

(Continued)

*Primary Examiner* — Eduardo C Robert
*Assistant Examiner* — Michelle C Eckman
(74) *Attorney, Agent, or Firm* — Skaar Ulbrich Macari, P.A.

(57) ABSTRACT

A bi-directional mechanically deployed rod mechanism utilizes non-parallel cam surfaces with a unique engagement, entrapment, and release methodology. The instrument utilizes a unique spring loading pivot point and lockout mechanisms to prevent early release of the pivot point and bi-directional cam surfaces.

8 Claims, 4 Drawing Sheets

(56) References Cited

U.S. PATENT DOCUMENTS

| | | | |
|---|---|---|---|
| 2011/0152952 A1* | 6/2011 | Oh | A61B 17/7085 606/86 A |
| 2011/0166610 A1* | 7/2011 | Altarac | A61B 17/708 606/86 A |
| 2011/0184464 A1* | 7/2011 | Fiorella | A61B 17/7089 606/264 |
| 2011/0196426 A1* | 8/2011 | Peukert | A61B 17/7083 606/279 |
| 2011/0218581 A1* | 9/2011 | Justis | A61B 17/708 606/86 A |
| 2011/0313463 A1* | 12/2011 | McLean | A61B 17/708 606/279 |
| 2012/0029580 A1* | 2/2012 | Solitario, Jr. | A61B 17/7083 606/86 A |
| 2012/0130429 A1* | 5/2012 | Mitchell | A61B 17/7004 606/259 |
| 2012/0179214 A1* | 7/2012 | Geist | A61B 17/7002 606/86 A |
| 2012/0271355 A1* | 10/2012 | Steele | A61B 17/7008 606/264 |
| 2013/0172937 A1* | 7/2013 | Davenport | A61B 17/7032 606/278 |
| 2014/0039567 A1* | 2/2014 | Hoefer | A61B 17/708 606/86 A |
| 2014/0046388 A1* | 2/2014 | Reichen | A61B 17/7083 606/86 A |
| 2014/0074106 A1* | 3/2014 | Shin | A61B 17/7079 606/104 |
| 2014/0088647 A1* | 3/2014 | Baynham | A61B 17/7004 606/246 |
| 2014/0100613 A1* | 4/2014 | Iott | A61B 17/7083 606/279 |
| 2014/0249592 A1* | 9/2014 | Black | A61B 17/7004 606/86 A |
| 2014/0277166 A1* | 9/2014 | Brinkman | A61B 17/7085 606/279 |
| 2014/0277197 A1* | 9/2014 | Brown | A61B 17/7086 606/86 A |
| 2015/0051653 A1* | 2/2015 | Cryder | A61B 17/7004 606/86 A |
| 2015/0066042 A1* | 3/2015 | Cummins | A61B 17/7037 606/104 |

\* cited by examiner

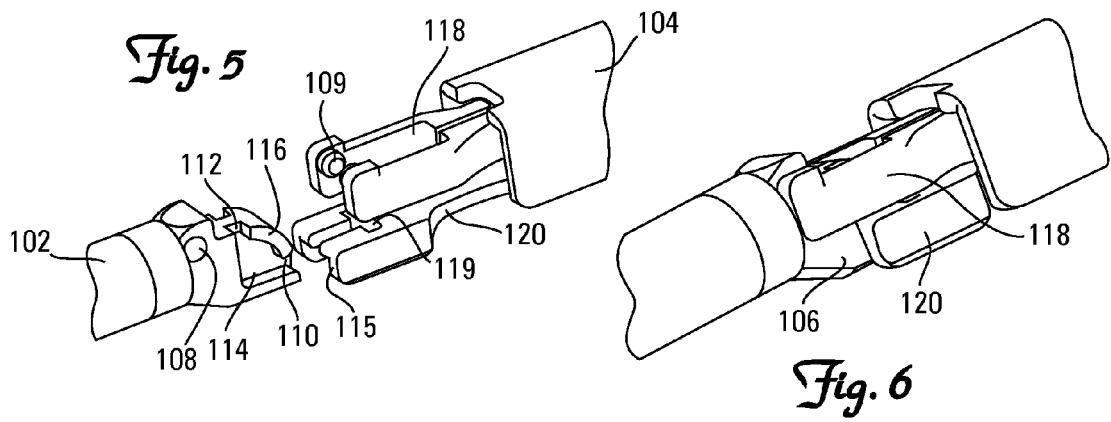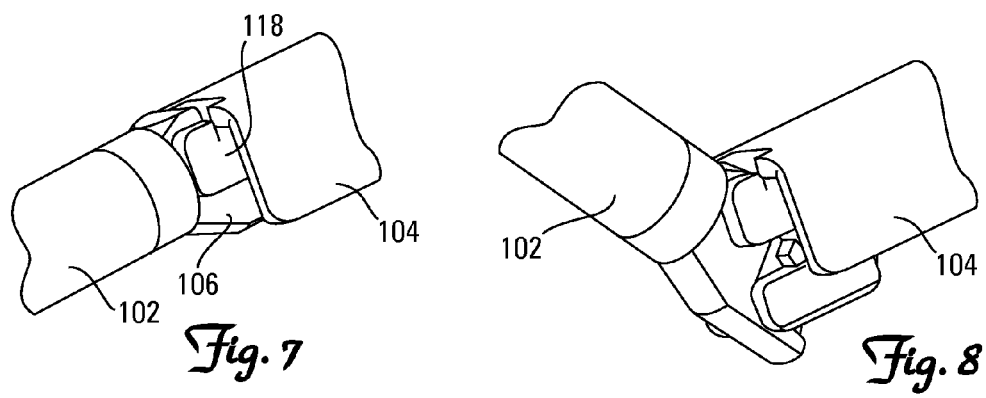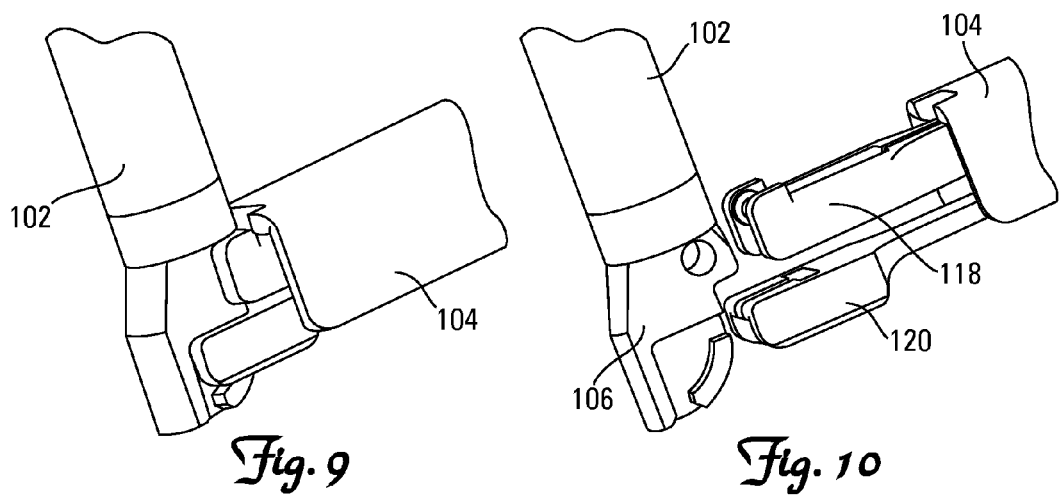

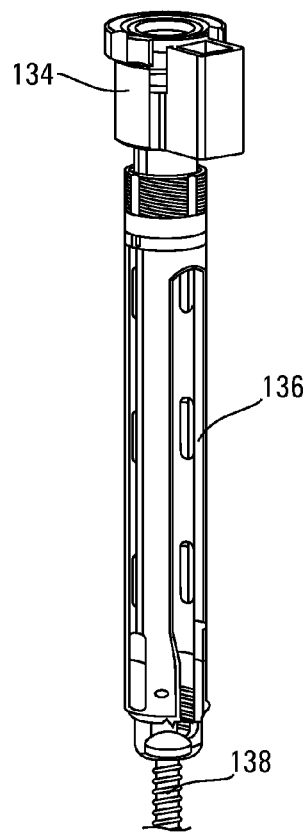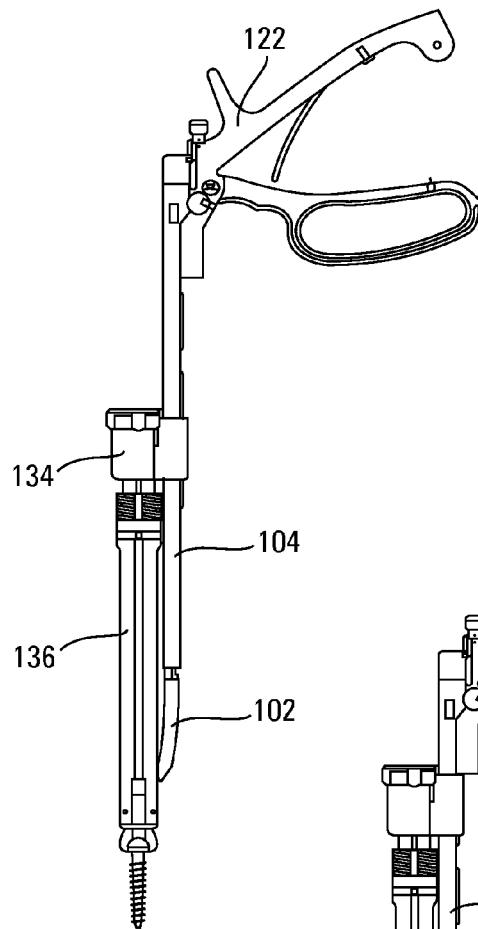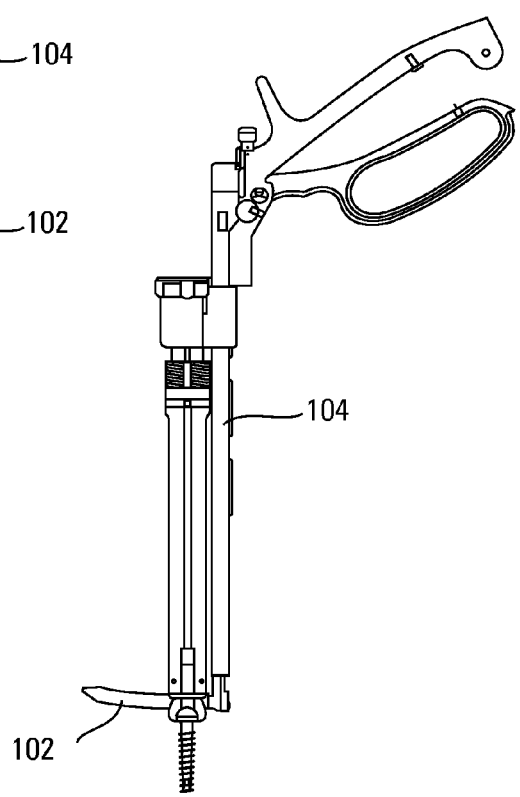
Fig. 13
Fig. 14
Fig. 15

ARTICULATING ROD HOLDER

PRIORITY

This application claims the benefit of U.S. Provisional Application Ser. No. 61/891,745, filed on Oct. 16, 2013, which is hereby incorporated herein by reference in its entirety.

FIELD

The present invention generally relates to spinal fusion surgeries. More particularly, the present invention relates to articulating rod holders for use in spinal fusion surgeries.

BACKGROUND

Pedicle screws and rod constructs are typically used for posterior fixation of vertebral bodies in spinal fusion surgeries. When spinal fusions are performed percutaneously, each screw may be attached to a temporary extension tubular device with slots generally timed to the screw slots which are designed for rod seating. Various rod holding devices exist to place the rods percutaneously into the extension slots and subsequently into the screw slots. These devices generally require extensive manipulation and the elongation of the surgical incision. Articulating rod holders allow rod insertion parallel to the extensions with mechanical rotation to a perpendicular position to the extensions for final seating.

Existing technology for articulating rod holders use either a one way cam whereby mechanical rotation from parallel to perpendicular is unidirectional and reversal cannot be mechanically activated/driven, or by parallel cams for bidirectional mechanical deployment. Each methodology has limitations.

SUMMARY

Disclosed is a new bi-directional mechanically deployed rod mechanism design that utilizes non-parallel cam surfaces with a unique engagement, entrapment, and release methodology. The instrument disclosed herein also utilizes a unique spring loading pivot point and lockout mechanisms to prevent early release of the pivot point and bi-directional cam surfaces.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

BRIEF DESCRIPTION OF THE DRAWINGS

FIGS. 5-10 depict an embodiment of the invention having an independent rod with its pivot point and forward cam driving point, cam driver entrance point, exit point, and reversal retention arc according to certain embodiments of the invention.

FIGS. 13-15 depict an embodiment of the instrument of the present invention having a guide in place.

DETAILED DESCRIPTION

Figure 1:
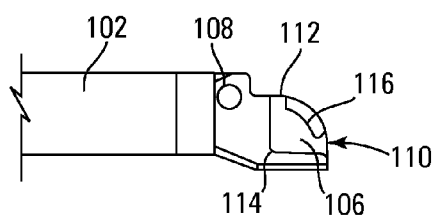
FIGS. 1-4 depict an embodiment of the non-parallel cam surfaces with a unique engagement, entrapment, and release methodology according to certain embodiments of the invention.

In the following descriptions, the present invention will be explained with reference to example embodiments thereof. However, these embodiments are not intended to limit the present invention to any specific example, embodiment, environment, applications or particular implementations described in these embodiments. Therefore, description of these embodiments is only for purpose of illustration rather than to limit the present invention. It should be appreciated that, in the following embodiments and the attached drawings, elements unrelated to the present invention are omitted from depiction; and dimensional relationships among individual elements in the attached drawings are illustrated only for ease of understanding, but not to limit the actual scale.

Referring to FIGS. 1-4, an embodiment of the non-parallel cam surfaces with a unique engagement, entrapment, and release methodology of the invention are shown in side views. The articulating rod holder 100 generally comprises a rod 102 and a driver 104. The rod includes a rod interface 106 disposed on an end thereof.

The rod interface 106 extends outwardly from the end of the rod and defines a pivot point 108 adjacent to the rod end. The interface also defines a cam driver entrance 110 in a horizontal or longitudinal direction, an exit 112 in a vertical or lateral direction, and forward pivot point 114 defined at the intersection of the entrance and exit planes. A cam driver reverse retention arc 116 is defined in the interface diagonally across the pivot point and longitudinally between the entrance and exits.

Figure 2:
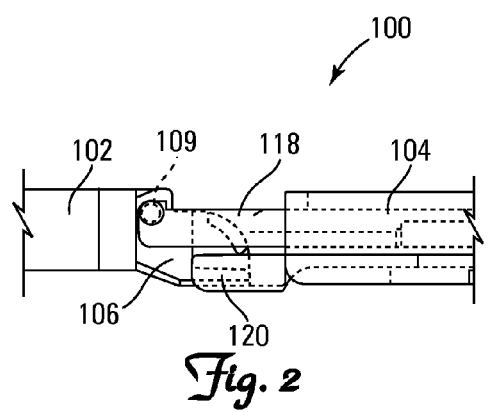

As shown in FIG. 2, the driver cam engagement projections 118 and 120 extending from an end of the driver 104 features are engaged with the rod interface 106. In particular, the pivot member 118 is engaged with the pivot point 108 and the driver cam 120 is engaged with the cam driver region of the interface. In the depicted orientation, the rod and driver are longitudinally aligned such that the driver cam 120 is in the load position.

Figure 3:
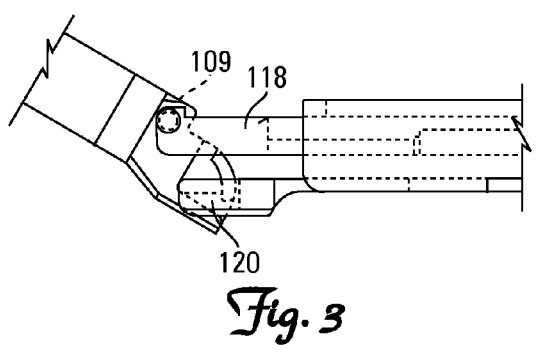

In FIG. 3, the rod 102 is pivoted until it is oriented at an oblique angle with respect to the longitudinal axis of the driver 104. In this orientation the driver cam 120 is entrapped for push/pull forces between the retention arc 116 and pivot point 114.

Figure 4:
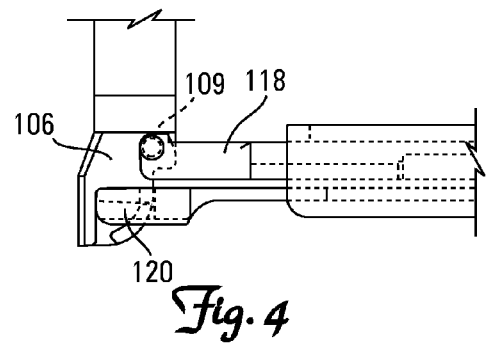

In FIG. 4, the rod 102 is pivoted until it is oriented at a right angle with respect to the longitudinal axis of the driver 104. In this orientation the driver cam 120 is in the unload/removal configuration.

FIGS. 5-10 illustrate various structural and operational aspects of certain embodiments in perspective view. In FIG. 5, the rod 102 includes the rod or female pivot point 108, cam driver entrance 110, cam driver exit 112, and cam driver pivot point 114. However, now can be more clearly seen various structures of the drive members 118 and 120.

In particular, the driver pivot member 118 includes a male driver pivot projection 109 adjacent a distal end of the pivot projection 118 for engagement with respective female pivot depressions 108. The driver cam member 120 defines a driver pivot point 115 at a distal end of the cam member 120, for engaging the respective cam surfaces of the rod interface

106. Also, a driver reverse retention channel 119 is defined in the drive member 120 proximally of the driver pivot point 115 in order to engage the inner surface of the reverse retention arc 116.

In FIG. 6, the rod and driver are shown to be engaged while in longitudinal alignment similar to that shown in FIG. 2. This is an "unlocked" position.

In FIG. 7, the "locked" position is shown. Here, drive members 118 and 120 are retracted longitudinally into the driver 104, while engaged with the rod 102 as shown in FIG. 6 such that the rod and driver move towards one another. Thus, this embodiment differs from that of FIGS. 1-4 in that the drive members are spring loaded to be extended during installation and connection with the rod interface 106.

FIGS. 8 and 9 depict the rod 102 pivoted with respect to the longitudinal axis of the driver 104 in an oblique angle (FIG. 8) and right angle (FIG. 9). In both orientations, the rod and driver remain in a "locked" position.

FIG. 10 depicts the drive members 118 and 120 now extended to the "unlocked" position and disengaged with the rod interface 106.

In certain embodiments, the drive members 118, 120 may be closed by a sliding collar, or other equivalent mechanism which slides, over at least a portion of the rod interface.

The driver cam 120 in certain embodiments has a longitudinal length from the driver pivot point 115 to the reverse retention slot 119 such that while the cam 120 is entrapped between the rod pivot point 114 and reverse retention arc 116, both forward and reverse articulation occurs along the longitudinal axis. At full 90 degree articulation, cam driver 120 aligns with the cam driver exit 112. The retention sleeve, collar or other retention mechanism is retracted to disengage the respective pivot points 108 and 109, and the rod 102 is removed.

Figure 11:
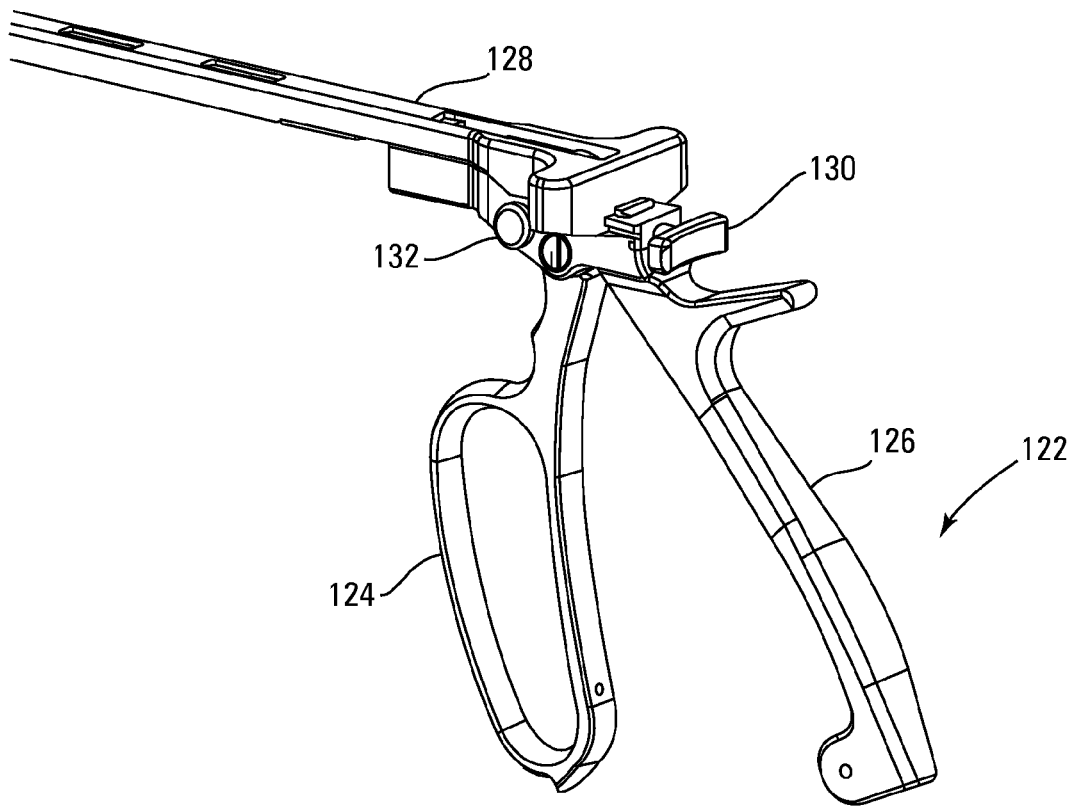
FIG. 11 depicts an embodiment of an articulating rod handle according to an embodiment of the invention.

FIG. 11 depicts an embodiment of an articulating rod handle 122. In one example embodiment, a movable handle 124 is be spring loaded with respect to a fixed handle 126. The movable handle 124 is moved by application of force towards the fixed handle 126 to articulate the rod 102 with respect to the driver. Releasing the force applied to the movable handle 124 reverses the rod articulation.

According to one example embodiment, the handle mechanism 122 includes a locking sleeve actuator 128 or other mechanism to retract the drive members 118 and 120 into the driver (or to extend a locking collar or other mechanism over the rod interface 106). Such action may be achieved by cam surfaces on both sides of at least one of the drive members which engage the locking sleeve. The cam surfaces may slide against the locking sleeve driving the members to the closed position by forward positioning. A release button 130 can be provided to return the locking sleeve (or reverse the retraction) to the unlocked position.

A means, such as a slide lock button 132, can be provided to the handle assembly 122 to lock the movement of the movable handle 124 in any position of its travel. When the slide lockout button 132 is engaged, the movable handle 124 is restricted or frozen in place such that the cam member 120 is prevented from withdrawing from the exit slot of the rod. This action may result in mechanical forward and reverse rod articulation between zero degrees (rod parallel to the device shaft) to about 88 degrees from parallel in certain embodiments.

The rod 102 may be loaded into the handle assembly 122, which includes the driver 104, by the user pushing the locking sleeve release button in, dropping a retention bar, thus allowing the locking sleeve to be pulled back. Such action moves the drive members to spring into the open position. The user may then slide the rod into the distal pivot points 108 and engage the drive cam 120 until the driver members 118 and 120 seat into the rod interface 106 simultaneously. Next the locking sleeve may be slid forward (or members retracted) to lock the pivot projections 109 into the rod pivot depressions 108 and engaging the locking sleeve member 128 of the handle assembly 122.

For final positioning and seating of the rod into a screw saddle at about 90 degrees of rod articulation, the lock out button 132 may be pushed in, releasing the movable handle 124 to a fully closed, 90 degree rod articulation position. When the movable handle 124 is released and returned to the non-articulated position by handle spring force, a driving bar connecting the handle 124 to the rod 102 withdraws out of a rod exit slot.

With the driving bar withdrawn from the rod exit slot, final release of the rod may require the rod and pivot member 118 points to be released. The user may push the locking sleeve release button 130, dropping the associated retention bar, and pull back the jaw locking sleeve. Then the pivot points are released by retracting the pivot member away from the rod pivot points 108.

Figure 12:
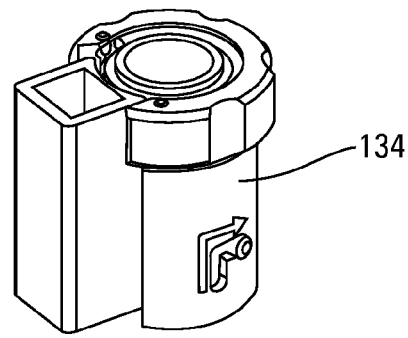
FIG. 12 depicts an embodiment of a rod holder guide according to the invention.

FIG. 12 depicts an example embodiment of a rod holder guide 134.

FIG. 13 depicts the instrument 100 of the present invention including the guide 134 engaged with a tower assembly 136. The tower assembly engages a screw assembly 138. The guide 134 may be attached to the tower assembly similarly to the pivot member 118 and rod interface described preciously.

As shown in FIG. 14, the tower assembly 134 is engaged with the handle assembly 122, which is in the locked position. FIG. 15 depicts the same device as FIG. 14, but now the driver is unlocked and the rod is articulated to a right angle with respect to the longitudinal axis of the driver.

The articulating rod 102 may be inserted through the guide 134 to keep the rod orientation parallel to the extension direction, maintain the rod's alignment with the slot in the extension and to define the final depth of extension.

The present invention may be embodied in other specific forms without departing from the spirit or essential attributes thereof, and it is, therefore, desired that the present embodiment be considered in all respects as illustrative and not restrictive. Those skilled in the art may recognize other equivalents to the specific embodiment described herein which equivalents are intended to be encompassed by the claims attached hereto.

What is claimed is:

1. A bi-directional mechanically deployed rod mechanism, comprising:
   a rod comprising a rod interface projecting from an end of the rod; and
   a driver comprising:
      a spring loaded pivot member extending from an end thereof, the spring loaded pivot member pivotally engaging a respective pivot point of the rod interface; and
      a spring loaded cam member extending from an end thereof, the spring loaded cam member defining a distal pivot point and a reverse retention slot,
   wherein the rod interface includes:
      a cam member entrance;
      a cam member exit defined in a non-parallel orientation with respect to the cam member entrance; and a cam member retention arc disposed between the cam member entrance and the cam member exit, the cam member retention arc defining an inward-facing curved surface.

2. The mechanism of claim 1, wherein the cam member entrance is perpendicular to the cam member exit.

3. The mechanism of claim 1, wherein the rod interface further comprises a pair of female pivot depressions to engage a pair of corresponding male projections defined on the spring loaded pivot member.

4. The mechanism of claim 1, wherein each of the a spring loaded pivot member and a spring loaded cam member move proximally and distally along a longitudinal axis of the driver between an extended position and a retracted position.

5. The mechanism of claim 4, wherein the spring loaded pivot member is separately movable with respect to the spring loaded cam member.

6. The mechanism of claim 1, wherein the rod interface further comprises a forward pivot point, wherein the cam member retention arc is spaced apart from the forward pivot point sufficient to allow the distal pivot point of the spring loaded cam member to span between the forward pivot point and the inward-facing curved surface of the reverse retention slot.

7. The mechanism of claim 1, wherein the reverse retention slot of the spring loaded cam member is located such that the cam member retention arc is extendable through the reverse retention slot as the rod is pivoted with respect to the driver.

8. The mechanism of claim 1, further comprising a lockout mechanism to prevent disengagement of the spring loaded pivot member and the spring loaded cam member from the rod interface.

* * * * *